US011572330B2

(12) United States Patent
Chouzier et al.

(10) Patent No.: US 11,572,330 B2
(45) Date of Patent: Feb. 7, 2023

(54) METHOD FOR OXIDATION OF CYCLOALKANES

(71) Applicant: BASF SE, Ludwigshafen am Rhein (DE)

(72) Inventors: Sandra Chouzier, Deaux (FR); Sergio Mastroianni, Lyons (FR); Avelino Corma, Valencia (ES); Mercedes Boronat, Vallada (ES); Javier Tirso Lopez Ausens, Sabinanigo (ES)

(73) Assignee: BASF SE

( * ) Notice: Subject to any disclaimer, the term of this patent is extended or adjusted under 35 U.S.C. 154(b) by 174 days.

(21) Appl. No.: 16/965,694

(22) PCT Filed: Jan. 28, 2019

(86) PCT No.: PCT/EP2019/051981
§ 371 (c)(1),
(2) Date: Jul. 29, 2020

(87) PCT Pub. No.: WO2019/149653
PCT Pub. Date: Aug. 8, 2019

(65) Prior Publication Data
US 2021/0040025 A1 Feb. 11, 2021

(30) Foreign Application Priority Data
Jan. 30, 2018 (EP) .................................. 18305084

(51) Int. Cl.
| C07C 45/28 | (2006.01) |
| C07C 45/51 | (2006.01) |
| C07C 51/31 | (2006.01) |
| C07C 29/48 | (2006.01) |
| C07C 45/53 | (2006.01) |

(52) U.S. Cl.
CPC .............. *C07C 51/31* (2013.01); *C07C 29/48* (2013.01); *C07C 45/53* (2013.01); *C07C 2523/52* (2013.01); *C07C 2601/14* (2017.05)

(58) Field of Classification Search
CPC .......... C07C 45/28; C07C 45/51; C07C 49/48
See application file for complete search history.

(56) References Cited

U.S. PATENT DOCUMENTS

| 6,160,183 A * | 12/2000 | Druliner .................. B01J 23/52 568/360 |
| 9,708,238 B2 * | 7/2017 | Decampo ................ C07C 35/02 |
| 2006/0041172 A1 | 2/2006 | Pirutko et al. |
| 2013/0296604 A1* | 11/2013 | Alshammari ........ B01J 23/8933 502/330 |
| 2015/0175514 A1 | 6/2015 | Decampo et al. |

FOREIGN PATENT DOCUMENTS

| CN | 103641679 A | 3/2014 |
| EP | 0 300 852 A1 | 1/1989 |
| EP | 0 388 567 A1 | 9/1990 |
| SU | 882992 A1 | 11/1981 |
| WO | 2011/051642 A1 | 5/2011 |
| WO | WO 2014/015491 A1 | 1/2014 |

OTHER PUBLICATIONS

International Search Report dated Feb. 14, 2019 in PCT/EP2019/051981 filed Jan. 28, 2019.

* cited by examiner

*Primary Examiner* — Sikarl A Witherspoon
(74) *Attorney, Agent, or Firm* — Faegre Drinker Biddle & Reath LLP

(57) ABSTRACT

The present invention concerns a method of oxidizing a cycloalkane to form a product mixture containing a corresponding alcohol and ketone, said method comprising contacting the cycloalkane with a hydroperoxide compound in the presence of a heterogenous catalyst comprising gold.

13 Claims, No Drawings

METHOD FOR OXIDATION OF CYCLOALKANES

FIELD OF THE INVENTION

The present invention concerns a method of oxidizing a cycloalkane to form a product mixture containing a corresponding alcohol and ketone, said method comprising contacting the cycloalkane with a hydroperoxide compound in the presence of a heterogeneous catalyst comprising gold.

BACKGROUND

The liquid phase aerobic oxidation of cyclohexane to a mixture of cyclohexanone and cyclohexanol, called K/A-oil, is a relevant process in the chemical industry. Cyclohexanol and cyclohexanone are precursors of adipic acid and caprolactam, which are key intermediates in the production of nylon-6 and nylon-6,6 polyamides. The first step in this process is the thermal air oxidation of cyclohexane to cyclohexyl hydroperoxide (CyOOH). Then, this hydroperoxide is decomposed to the K/A-oil according to the following scheme (1):

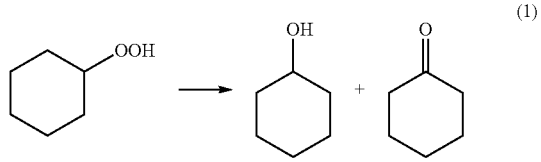

(1)

This deperoxidation step is currently catalyzed either by an aqueous solution of NaOH containing $Co^{2+}$ cations or by an organic solution containing $Cr^{6+}$ compounds but it is becoming necessary, for environmental reasons, to replace such homogeneous processes with new non-toxic heterogeneous catalytic systems.

Most efforts up to the moment have focused on the use of metal exchanged molecular sieves, polymer and silica-supported transition metal complexes, or transition metal oxides and hydroxides. While some of these materials show relatively good activities and selectivities to K/A-oil, most of them suffer from deactivation and/or metal leaching, thus preventing their industrial application.

Gold catalysts are known to carry out the deperoxidation reaction.

SUMMARY OF THE INVENTION

The main reaction is the dehydration of CyOOH to cyclohexanone (reaction (a), scheme (2) below). The inventors found that, in the deperoxidation process, it is possible to use the oxygen in the hydroperoxide to simultaneously oxidize the alkane solvent (reaction (b), scheme 2), thus obtaining selectivities to K/A-oil larger than 100%. Such selectivities have been reported for homogeneous catalysts containing Ru and Os. Favoring reaction (b) is of great interest as it enables to improve the yield of K/A-oil. It was further found that favorable conversion and efficiency can be achieved when using a gold catalyst with a metal oxide as a support.

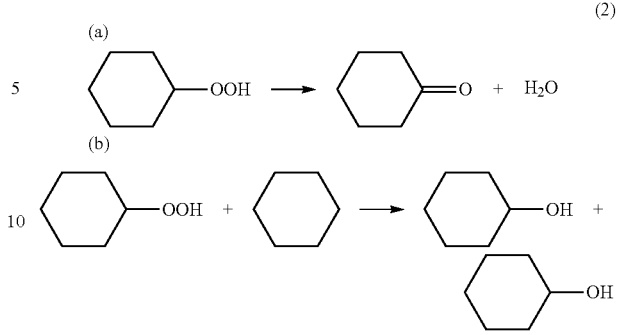

(2)

The present invention therefore relates to the subject matter defined in the following items 1 to 27:

1. A method of oxidizing a cycloalkane to form a product mixture containing a corresponding alcohol and ketone, the method comprising contacting the cycloalkane with an hydroperoxide compound in the presence of a heterogeneous catalyst comprising gold supported on an oxide, wherein the oxidation takes place in a reaction mixture comprising the cycloalkane and the hydroperoxide at a temperature in the range from 80° C. to 110° C.

2. The method of item 1, wherein the heterogeneous catalyst is present in a catalytically effective amount.

3. The method of item 1 or 2, wherein the cycloalkane is cyclohexane, the corresponding alcohol is cyclohexanol, and the corresponding ketone is cyclohexanone.

4. The method of any one of the preceding items, wherein the hydroperoxide compound is selected from the group consisting of tert-butyl hydroperoxide, tert-amyl hydroperoxide, cumene hydroperoxide, ethylbenzene hydroperoxide, cyclohexyl hydroperoxide, methylcyclohexyl hydroperoxide, tetrahydronaphtalene hydroperoxide, isobutylbenzene hydroperoxide, ethylnaphthalene hydroperoxide and combinations thereof.

5. The method of any one of the preceding items, wherein the hydroperoxide compound is cyclohexyl hydroperoxide or tert-butylhydroperoxide.

6. The method of any one of the preceding items, wherein the hydroperoxide compound is cyclohexyl hydroperoxide.

7. The method of any one of the preceding items, wherein the reaction temperature is within the range from 85° C. to 105° C.

8. The method according to any one of the preceding items, wherein the oxide is selected from the group consisting of $TiO_2$, ZnO, MgO, $CeO_2$ and $ZrO_2$.

9. The method according to any one of the preceding items, wherein the morphology of the oxide is selected from the group consisting of amorphous, cubic, octahedral, rod-like and combinations thereof.

10. The method of any one of the preceding items, wherein the mixture further comprises a radical scavenger.

11. The method of claim 10, wherein the radical scavenger is selected from the group consisting of hydroquinone, catechol, resorcinol, aminophenol, phenol, phenylenediamine, paramethoxyphenol and combinations thereof.

12. The method of claim 10 or 11, wherein the radical scavenger is hydroquinone.

13. The method of any one of the preceding items, wherein less than 7 wt.-%, preferably less than 6 wt.-%, more preferably less than 5 wt.-% of byproducts is formed during the reaction.

14. The method of any one of the preceding items, wherein the product mixture comprises less than 7 wt.-%, preferably less than 6 wt.-%, more preferably less than 5 wt.-% of byproducts.

15. The method of any one of the preceding items, wherein the diameter of the gold particles is within the range from 0.5 nm to 20 nm.

16. The method of any one of the preceding items, wherein the diameter of the gold particles is within the range from 1 nm to 15 nm.

17. The method of any one of the preceding items, wherein the diameter of the gold particles is within the range from 2 nm to 10 nm.

18. The method of any one of the preceding items, wherein the heterogeneous catalyst comprises 0.01 to 10 wt.-% of gold, based on the total weight of the heterogeneous catalyst.

19. The method of any one of the preceding items, wherein the heterogeneous catalyst comprises 0.1 to 8 wt.-% of gold, based on the total weight of the heterogeneous catalyst.

20. The method of any one of the preceding items, wherein the heterogeneous catalyst comprises 0.2 to 5 wt.-% of gold, based on the total weight of the heterogeneous catalyst.

21. The method according to any one of the preceding items, wherein the conversion of the reaction is in the range from 50 to 100%.

22. The method according to any one of the preceding items, wherein the conversion of the reaction is in the range from 90 to 100%.

23. The method of any one of the preceding items, wherein the efficiency of the reaction is greater than 100%.

24. The method of any one of the preceding items, further comprising oxidizing the cyclohexanol/cyclohexanone mixture to adipic acid, with nitric acid.

25. The use of a heterogeneous catalyst comprising gold supported on an oxide for converting a cycloalkane into the corresponding cycloalkanol.

26. The use of a heterogeneous catalyst comprising gold supported on an oxide for oxidizing a cycloalkane.

27. The use of of item 25 or 26, comprising a method as defined in any one of claims 1 to 24.

DETAILED DESCRIPTION

The present invention relates to a method of oxidizing a cycloalkane to form a product mixture containing a corresponding alcohol and ketone. The method comprises contacting the cycloalkane with a hydroperoxide compound in the presence of a heterogeneous catalyst comprising gold supported on an oxide, e.g. a metal oxide. The oxidation takes place in a reaction mixture comprising the cycloalkane and the hydroperoxide at a temperature in the range from 80° C. to 110° C.

The term "cycloalkane" as used herein refers to saturated cyclic hydrocarbons. The cycloalkane typically has from 3 to about 12 carbon atoms, preferably from 3 to about to 10 carbon atoms; still more preferably from about 5 to about 8 carbon atoms. Non-limiting examples of cycloalkanes include cyclopentane, cyclohexane, cycloheptane, and cyclooctane. Cycloalkane can also be cyclodecane, cyclododecane or decaline. In a preferred embodiment, cycloalkane is cyclohexane.

The phrase "corresponding alcohol and ketone" means a cycloalkanol and a cycloalkanone, respectively, having the same number of carbon atoms as the cycloalkane from which it is derived, without additional modifications. For example, if the cycloalkane is cyclohexane, then the corresponding alcohol is cyclohexanol, and the corresponding ketone is cyclohexanone. If the cycloalkane is cyclooctane, then the corresponding alcohol is cyclooctanol, and the corresponding ketone is cyclooctanone.

Hydroperoxide compounds according to the present invention may be for example hydrogen hydroperoxide or an organic hydroperoxide.

Specific examples of the hydroperoxide compounds which are usable in the present invention may be represented by the formula (I) as follows:

wherein R is a hydrocarbon group that may comprise from 1 to 15 carbon atoms, mainly alkyl or aryl groups.

As used herein, the term "hydrocarbon group" refers to a group consisting of carbon atoms and hydrogen atoms, which group may be saturated or unsaturated, linear, branched or cyclic, aliphatic or aromatic. Hydrocarbon groups of the present invention may be alkyl groups, alkenyl groups, or aryl groups.

Alkyl as used herein means a straight chain or branched saturated aliphatic hydrocarbon. As used herein, unless stated otherwise, the term "alkyl" means a linear or branched alkyl group optionally substituted with one or more substituent selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

Aryl as used herein means a 6-carbon monocyclic or 10-carbon bicyclic aromatic ring system wherein 0, 1, 2, 3, or 4 atoms of each ring are substituted by a substituent, such as O or N. Examples of aryl groups include phenyl, naphthyl and the like.

Hydroperoxides are preferably chosen in the group consisting of: tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin (i.e., tetrahydronaphtalene) hydroperoxide, isobutylbenzene hydroperoxide, and ethylnaphthalene hydroperoxide.

More preferably hydroperoxides are alkyl hydroperoxides such as tert-butyl hydroperoxide or cyclohexyl hydroperoxide.

These hydroperoxides may also be used in combination of two or more species thereof.

The hydroperoxide compound is advantageously used in a solution in an alkane. Any alkane can be used with a preference for cyclohexane. The concentration of the peroxide compound in the solution in an alkane, preferably in cyclohexane, is advantageous comprised between 0.1 wt % and 50 wt %, preferably between 2 wt % and 15 wt %.

In a preferred embodiment, no other oxidant agent than the hydroperoxide compound of the invention is used for the process of the invention. Advantageously no further oxidant agent such as pure oxygen, air, oxygen-enriched or oxygen-depleted air or, alternatively, oxygen diluted with an inert gas, is used for the process of the invention.

The heterogeneous catalyst comprises gold on an oxide support, e.g. on a metal oxide support. The gold can be supplied in any suitable form. For example, it can be deposited onto the support by impregnation, precipitation, deposition-precipitation, ion-exchange, anion or cation adsorption from solutions, and vapor phase deposition. In addition, gold containing catalysts can be prepared by introducing the source of gold at the stage of hydrothermal synthesis, of the support material. When using the abovementioned and other possible methods, the amount of introduced gold is varied in a wide range up to about 10 wt %. Preferred amounts are in the range of from about 0.1 wt.-% to about 8 wt.-%, or from about 0.2 wt.-% to about 5 wt.-%.

The catalyst typically contains ultrafine sized gold particles from about 0.5 nm to about 20 nm in diameter, preferably from about 1 nm to about 15 nm, more preferably from about 2 nm to about 10 nm.

The oxide is preferably selected from $TiO_2$, ZnO, MgO, $CeO_2$ and $ZrO_2$. The oxides can be provided as described in the examples hereinbelow. Further methods for synthesis of the oxides are known to the skilled person.

The oxide may have any morphology. If the oxide is cerium oxide, the preferred morphologies include, but are not limited to, amorphous, cubic, octahedral, rod-like and combinations thereof.

The reaction mixture may further comprise a scavenger which leads to a reduction in by-products. Preferred scavengers include, but are not limited to, hydroquinone, catechol, resorcinol, aminophenol, phenol, phenylenediamine, paramethoxyphenol and combinations thereof. Hydroquinone is the preferred scavenger.

Preferably, less than 7 wt.-%, or less than 6 wt.-%, more preferably less than 5 wt.-% of byproducts is formed during the reaction. The product mixture preferably contains less than 7 wt.-%, or less than 6 wt.-%, more preferably less than 5 wt.-% of byproducts. Byproducts include, for example, carboxylic acids, diols, lactones, peroxide.

Preferably, the method of the invention results in a good conversion. Conversion is defined as the ratio between the number of moles of hydroperoxide ROOH transformed divided by the number of initial moles of ROOH.

$$\text{Conversion}(\%) = 100 \times \frac{nROOH \text{ (consumed)}}{nROOH \text{ (initial)}}$$

Preferred conversion of the method of the invention is in the range from 50% to about 100%, or from 60% to about 100%, or from 70% to about 100%, or from 80% to about 100%, or from 90% to about 100%. In other embodiments, the conversion is in the range from 50% to less than 100%, or from 60% to less than 100%, or from 70% to less than 100%, or from 80% to less than 100%, or from 90% to less than 100%.

The method of the invention further provides good selectivities. The terms "selectivity" and "efficiency" are used synonymously herein. In the case of tBuOOH decomposition, efficiency is defined as the number of moles of Cyclohexanol (CyOH) and cyclohexanone (CyO) produced divided by the number of moles of tBuOOH consumed.

$$\text{Efficiency}(\%) = 100 \times \frac{nCyOH \text{(produced)} + nCyO \text{ (produced)}}{ntBuOOH \text{ (consumed)}}$$

If efficiency is 0, catalyst decomposes tBuOOH without oxidizing cyclohexane. If efficiency is higher than 0, catalyst is able to decompose the peroxide and oxidise cyclohexane at the same time.

In the case of CyOOH decomposition, efficiency is defined as the number of moles of Cyclohexanol (CyOH) and cyclohexanone (CyO) produced divided by the number of moles of CyOOH consumed.

$$\text{Efficiency}(\%) = 100 \times \frac{nCyOH \text{ (produced)} + nCyO \text{ (produced)}}{nCyOOH \text{ (consumed)}}$$

When efficiency is lower or equal to 1, catalyst only decomposes CyOOH without oxidizing cyclohexane. When efficiency is higher than 1, catalyst is able to decompose the peroxide and oxidise cyclohexane at the same time.

Preferred efficiencies of the method of the invention are from about 80% to about 125%, or from about 90% to about 120%, or from about 100% to about 115%.

In the practice of the invention, the catalysts can be contacted with a cycloalkane, such as cyclohexane, and a hydroperoxide in a fixed bed, which is arranged to provide intimate contact between the catalyst and reactants. Alternatively, catalysts can be slurried with reaction mixtures using techniques known in the art. The process of the invention is suitable for either batch or continuous cycloalkane oxidation. These processes can be performed under a wide variety of conditions, as will be apparent to persons of ordinary skill.

Suitable reaction temperatures for the process of the invention range from 80 to 110° C., advantageously from about 85 to about 105° C., preferably from about 90 to about 105° C., more preferably from about 95 to about 105° C.

The process according to the invention is performed advantageously at a pressure from 0.1 MPa (1 bar) to 2 MPa (20 bar), preferably from 0.1 MPa (1 bar) to 1 MPa (10 bar) and more preferably from 0.1 MPa (1 bar) to 0.3 MPa (3 bar).

Cycloalkane reactor residence time generally varies in inverse relation to reaction temperature, and typically is comprised between 30 and 1440 minutes.

The catalysts of the present invention may be recovered, and regenerated by a conventionally known method. More specifically, the catalyst may be regenerated so that it recovers an initial activity, for example, by recovering and drying the catalyst, or by calcining the catalyst in air.

At the end of the reaction, the compound of interest may be eventually purified by well known methods of the technical field, such as distillation.

Should the disclosure of any of the patents, patent applications, and publications which are incorporated herein by reference conflict with the description of the present application to the extent that it may render a term unclear, the present description shall take precedence.

Another aspect of the invention is the use of a heterogeneous catalyst comprising gold supported on an oxide for converting a cycloalkane into the corresponding cycloalkanol. Yet another aspect of the invention is the use of a heterogeneous catalyst comprising gold supported on an oxide for oxidizing a cycloalkane. The preferred embodiments of the use of the invention correspond to the preferred embodiments of the method of the invention described herein mutatis mutandis.

The following examples are provided for illustrative purposes only and should not be regarded as limiting the invention.

EXAMPLES

Materials And Methods

Analysis

Iodometry

Cyclohexyl hydroperoxide (CyOOH) was quantified by iodometry which consisted in reacting CyOOH with potassium iodide to yield cyclohexanol and iodine. The amount of iodine formed was estimated by potentiometry by reaction of iodine with sodium thiosulfate ($Na_2S_2O_3$). About 1 g of a solution containing CyOOH was weighed in an Erlenmeyer flask. Then, 20 mL of 80% acetic acid, about 1 g of sodium hydrogenocarbonate ($NaHCO_3$) and about 1 g of potassium iodide were introduced. $NaHCO_3$ is a weak base and reacts with acetic acid to produce carbon dioxide, so that oxygen was pushed away. Indeed, the presence of oxygen would induce error on the evaluation of the CyOOH quantity. After mixing, the Erlenmeyer flask was stored 20 minutes in the dark. The Erlenmayer flask was washed with distilled water and acetonitrile (which avoids the formation of foam). The solution was dosed with a solution of $Na_2S_2O_3$ (0.1 N) thanks to a potentiometer equipped with a Pt probe (ref 60451100 Metrohm). The same method is used to quantify tert-butyl hydroperoxide (tBut-OOH).

Gas Chromatography (GC)

GC used to Quantify Cyclohexanol, Cyclohexanone and CyOOH after CyOOH Decomposition The reaction mixture containing cyclohexane, CyOOH, cyclohexanol, cyclohexanone and small amounts of other byproducts (carboxylic acids . . . ) were quantified by GC using a specific polar column (Permabond FFAP length 20 m, film thickness 0.10 µm) after calibration with different CyOOH solutions of known concentrations established by iodometry.

GC used to Quantify Cyclohexanol and Cyclohexanone formed after tBuOOH Decomposition The reaction mixture contains cyclohexane, tert-butyl hydroperoxide, cyclohexanol, cyclohexanone, tert-butanol and small amounts of other byproducts, like carboxylic acids or diols.

Tert-butyl hydroperoxide is quantified by iodometry, while cyclohexanol and cyclohexanone formed during the reaction are quantified by GC using a Varian CP-3800 chromatograph with a HP-5 column (0.25 µm film thickness, length 25 m, inner diameter 0.25 mm). For each sample, 30 µL are extracted from the glass reactor vessel using a syringe and introduced in a vial containing cyclohexane. The amount of tBuOOH is measured by iodometry.

Determination of Particle Size by Electron Microscopy

Transmission electron microscopy (TEM) is used for measuring particle size of Au supported catalyst particles. Some TEM images were collected using a JEOL DEBEN AMT JEM-1010 microscope operating at 100 kV, while other were taken using normal bright-field and High-angle Annular Dark Field Scanning Transmission Electron Microscopy. The images were acquired on a JEOL 2010 field emission gun transmission electron microscope operated at 200 kV.

Dinitrogen physisorption for BET area quantification was performed on a Micromeritics ASAP® 2420 Accelerated Surface Area and Porosimetry System at 77 K. BET analyses allowed to determine the surface area of the catalysts.

Materials

Cyclohexyl Hydroperoxide (CyOOH) Solution

CyOOH was extracted from a cyclohexane oxidate resulting from the thermal oxidation of cyclohexane by oxygen. The oxidate was extracted three times with 1 M NaOH (Merck) and the water phase was then neutralized with a chilled aqueous 4 M HCl (Merck, pro analysis, at least 99 wt %) solution until slightly acidic. The water phase was subsequently extracted 3 times with cyclohexane (Sigma Aldrich, 99%) and dried over $Na_2SO_4$ or $MgSO_4$ (Merck). Finally, 1% mol biphenyl (Acros, 99%) was added to the filtered solution as an internal standard for GC analysis and the solution was diluted with cyclohexane to concentrations ranging from 2-6 wt % CyOOH.

Tert-butyl Hydroperoxide (tBuOOH) Solution

A 70% tBuOOH/water solution was purchased from Aldrich. The solution was extracted with cyclohexane to get a tBuOOH/cyclohexane solution. The title was adjusted to 7 wt % after titration by iodometry.

Catalysts (for Comparison)

$CeO_2$: this catalyst can be produced according to a process described in EP 300852 or EP 388567
Zirconium dioxide ($ZrO_2$): commercial product from Aldrich
Zinc oxide (ZnO): commercial product from Fluka
$TiO_2$: commercial product from Euro Support, product reference: Mirkat-411
Magnesium oxide (MgO 600 $m^2/g$): commercial product from Nanoactive
Alumina ($Al_2O_3$ 550 $m^2/g$): commercial product from Nanoactive.

Catalysts of the Invention $Au/TiO_2$: commercial product from Strem Chemicals
$Au/Al_2O_3$: commercial product from Strem Chemicals
Au/ZnO: commercial product from Strem Chemicals Synthesis of $Au/TiO_2$ 30 mL of an aqueous solution of $HAuCl_4$ is prepared and kept to pH=9, adjusted with NaOH 0.2M. Then 1 g of $TiO_2$ (as described above) is added and the solution stirred during 1 hour at 70° C. while keeping the pH constant. Then the solution is filtered and washed thoroughly with deionized water. After, it is dried at 80° C. overnight and reduced.
Two different reduction methods were tested:
Reduction with phenyl ethanol at 160° C. for 2 hours (10 mL of phenyl ethanol per gram of solid). After reduction, the solid is filtered, washed with water and then dried at 80° C.
Reduction with hydrogen: treatment under nitrogen flow during 3 hours at 450° C. followed by hydrogen treatment for 3 hours at 250° C.

Synthesis of $Au/CeO_2$ 1 g of $CeO_2$ (as described above) is added to 35 mL of ultrapure water and kept stirred. A second solution containing the Au precursor is prepared. 20 mg of $HAuCl_4$ are added to 2.42 mL of ultrapure water. The pH is adjusted to 10 thanks to the addition of NaOH 0.2M. This solution is then added to the $CeO_2$ aqueous solution. The resulting solution is kept stirring and pH is kept constant at 10 overnight. Then the solution is vacuum filter and washed with 2 L of deionized water. A test with $AgNO_3$ is made to ensure there is no remaining $Cl^-$ in the filtrate. The solid is finally washed with acetone, filtered and dried in air at 100° C. overnight. Then, the solid is reduced by phenyl ethanol at 160° C. for 2 hours (10 mL of phenyl ethanol per gram of solid). Then, the solid is washed with 1 L of distilled water, 100 mL of acetone and finally 100 mL of diethyl ether. Finally it is dried at 100° C. in air overnight.

Synthesis of Au/MgO

Two different Au precursors were used Au(III)acetate or Au(III)dimethyl acetyl acetonate.

The Au salt is dissolved in toluene and then MgO (as described above) is added to the solution. It is stirred overnight at room temperature. The solvent is then evaporated. The solid is calcined under $N_2$ for 3 hours at 450° C., then it is reduced under $H_2$ for 3 hours at 250° C.

Synthesis of $Au/ZrO_2$ 300 mL of a solution of $HAuCl_4$ and urea 0.5 M is prepared in ionized water and heated up to 80° C. 3 g of $ZrO_2$ (as described above) are then dispersed in the solution and the pH is adjusted to 8 with NaOH 0.2M. The solution is stirred for 4 hours keeping pH constant. Then the solid is filtered with hot deionized water and dried at room temperature for 24 hours. Finally, it is calcined at 250° C. for 2 hours in air flow.

Synthesis of Nanostructured Ceria

It was synthesized according to a method described in the literature using hydrothermal method. (S. Laursen et al., "First principle Design of Highly Active and Selective Catalysts for Phosgene-Free Synthesis of Aromatic Polyurethane", Angewandte Chemie International Edition 51.17 (2012), pp 4190-4193)

A solution of NaOH was added under vigorous stirring to a solution of $Ce(NO_3)_3 \cdot 6H_2O$ (Aldrich, Analytical grade). The formed suspension was kept stirring for 30 minutes. This step produces seeds for the hydrothermal growth. This milky slurry was transferred to a Teflon liner autoclave and the autoclave was sealed tightly. The autoclave was transferred to an oven for the hydrothermal treatment during 24 hours. Table 1 shows the conditions for each type of $CeO_2$ nano-structure. After cooling down at room temperature, the precipitated yellow-white solids were filtrated and washed thoroughly with distillated water, controlling the pH of the filtrates. After that, the samples were dried at 120° C., under flowing air for 12 hours.

TABLE 1

Synthesis parameters for the production of the CeO2 nano-structures.

| SHAPE | $V_{Sol \cdot NaOH}/V_{Sol \cdot Ce+3}$ | [NaOH] (M) | [Ce$^{+3}$] (M) | T (° C.) |
|---|---|---|---|---|
| Cubes | 7 | 9 | 5 | 200 |
| Octahedra | 7 | 1 | 5 | 175 |
| Rods | 7 | 9 | 5 | 100 |

The synthesis of $Au/CeO_2$ nano-structures catalysts was performed in the same manner as $Au/CeO_2$ as described above in "Synthesis of $Au/CeO_2$".

In order to characterize the ability of gold supported catalysts to oxidize alkanes by CyOOH, some tests were undertaken in a medium containing cyclohexane and Tert-butylhydroperoxide (tBuOOH). It is easier to discriminate oxidation products from peroxide decomposition production as K/A-oil formation is only due to cyclohexane oxidation.

General Conditions of tBuOOH and CyOOH Deperoxidation Reaction

Reactor. The reaction is performed in a batch reactor consisting of:
- a glass reactor vessel (chemical and thermal shock resistant, 2 mL Volume capacity, Duran Manufacturer).
- a vent valve (Gas inlet, for pressurizing/depressurizing the system with nitrogen).
- an outlet micro valve for sample taking.
- a pressure gauge (Pressure range: 1-16 bar).
- a magnetic stirring bar, which is stored inside the reaction media in the reactor vessel.

To ensure that the reactor is completely clean and no traces of contaminants are present, it is first washed with acetone, then with cyclohexane, and after that dry air is passed through.

Reaction Procedure

The proper amount (160 mg) of catalyst is introduced in the reactor, and possibly the radical scavenger. Then, 200 microL of internal standard Undecane (99% purity, from Sigma-Aldrich) are introduced in the glass reactor vessel and its exact mass weighted.

Next, the reactor is opened, 20 mL of the 7 wt % tert-butyl hydroperoxide/cyclohexane solution or cyclohexyle hydroperoxide/cyclohexane solution are introduced, and its exact mass weighted. Finally, a magnetic stir bar is introduced and the reactor is closed. An overpressure of nitrogen is then added in order to increase the boiling point of cyclohexane and keep reaction media at liquid state. The gas is introduced through the vent valve until an internal pressure in the reactor within 4 to 6 atmosphere is reached.

A silicon bath at the desired reaction temperature (100° C.) is kept on a hot-stirring plate. The stirring is set to 500 rpm. The glass reactor vessel is introduced in the bath, and the reaction starts.

To follow the reaction progress, samples are taken at different times and their composition analyzed by iodometry (t-butyl hydroperoxide) and Gas Chromatography (cyclohexanol and cyclohexanone and CyOOH). At each time, the reactor is first taken off the bath and stored in a water bath at room temperature, in order to cool down the reaction media. Once the reactor is at room temperature, three different samples are taken from it through the outlet micro valve and analyzed.

General Conditions of CyOOH Deperoxidation Reaction: (only for examples 33 and 34)

Reactor

The reaction is performed in a Teflon batch reactor consisting of:
- a teflon reactor vessel (40 mL Volume capacity, Bola Manufacturer)
- an outlet micro valve for sample taking.
- a pressure gauge.

a thermocouple a magnetic stirring bar, which is stored inside the reaction media in the reactor vessel.

To ensure that the reactor is completely clean and no traces of contaminants are present, it is first washed with acetone, then with water. In case some trace of metal remains on the reactor wall, it is washed with diluted HCl.

Reaction Procedure

The proper amount (160 mg) of catalyst is introduced in the reactor. Then, 0.6 g of internal standard orthodichlorobenzene (99% purity, from Sigma-Aldrich) are introduced in the teflon reactor.

Next, the reactor is opened, about 16 g of the CyOOH purified solution are introduced and its exact mass weighted. Finally, a magnetic stir bar is introduced and the reactor is closed.

A silicon bath at the desired reaction temperature (typically 100° C.) is kept on a hot-stirring plate. The glass reactor vessel is introduced in the silicon bath.

It takes about 30 minutes to reach 100° C. inside the reactor. During this transition period of heat, the stirring is off to slow down reaction between room temperature and 100° C.

The follow up of reaction and stirring of the mixture begin when temperature reaches 100° C. To follow the reaction progress, samples are taken at different times and their composition analyzed by Gas Chromatography. The medium is sampled through a syringe and put in a GC vial when it is cold.

Results

Firstly tests in tBuOOH/cyclohexane medium were made. One can thus discriminate more easily the product coming from the decomposition of the peroxide in acetone and tert-butanol and the oxidation products of cyclohexane to K/A-oil.

Examples 1 to 6 (According to the Invention)

First, the effect of the catalyst support in gold catalysis on both conversion and efficiency was tested.

It was observed that gold supported catalysts are able to oxidise cyclohexane. All catalysts have an efficiency in the range between 0.31 and 0.39 except Au/MgO which shows a low efficiency of 0.22.

All catalysts exhibited a similar activity except Au/ZnO which was less active.

TABLE 2

Catalytic performance of Au supported catalysts after 9 hours test in 7 wt % tBuOOH/cyclohexane medium

| Example | Catalyst | % Au (wt) | Au particle size (nm) | Conversion (%) | Efficiency (%) | K/A ratio |
|---|---|---|---|---|---|---|
| 1 | Au/TiO$_2$* | 1 | 2.5 | 98.7 | 39 | 0.91 |
| 2 | Au/Al$_2$O$_3$ | 1 | 2.5 | 98.5 | 35 | 0.91 |
| 3 | Au/ZnO | 1 | 2.5 | 60.9 | 31 | 0.69 |
| 4 | Au/CeO$_2$ | 1.15 | — | 100.0 | 35 | 0.93 |
| 5 | Au/MgO | 1.31 | 14.3 | 98.7 | 22 | 0.82 |
| 6 | Au/ZrO$_2$ | 1.02 | 2.2 | 100.0 | 35 | 0.84 |

*commercial catalyst

Examples 7 to 10 (Comparative Examples)

The tests of the supports showed that their catalytic activity is much lower compared to gold supported catalysts, showing activity mainly comes from the metal in the previous examples. These supports were calcined in air at 400° C. for 4h prior being tested.

TABLE 3

Catalytic performance of supports after 9 hours test in 7 wt % tBuOOH/cyclohexane medium

| Example | Catalyst | BET surface area (m$^2$/g) | Conversion (%) | Efficiency (%) | K/A ratio |
|---|---|---|---|---|---|
| 7 | TiO$_2$ | 262 | 17.94 | 24 | 0.58 |
| 8 | Al$_2$O$_3$ | 550 | 36.9 | 23 | 0.70 |
| 9 | ZnO | 40 | 9.4 | 25 | 0.60 |
| 10 | MgO | 600 | 10.8 | 28 | 0.59 |

Examples 11 to 16 (According to the Invention)

Then the impact of the increase of gold loading in Au/TiO$_2$ was evaluated. The following table shows that it does not modify significantly particle size which is around 6-7 nm. In terms of activity, the higher the amount of Au the higher the deperoxidation rate is. The catalysts with a lower amount of Au exhibit a lower ability to oxidize cyclohexane compared to catalysts with more Au.

TABLE 4

Catalytic performances of Au/TiO$_2$ catalysts with different gold loading after test in 7 wt % tBuOOH/cyclohexane medium

| Example | Au loading (% wt) | Au particle size (nm) | Conversion (%) | Efficiency (%) | K/A Ratio |
|---|---|---|---|---|---|
| 11 | 0.06 | 6.9 ± 2.8 | 57.3 | 15 | 0.90 |
| 12 | 0.32 | 7.9 ± 3.0 | 77.0 | 25 | 1.02 |
| 13 | 2.60 | 8.4 ± 2.8 | 93.2 | 31 | 1.04 |
| 14 | 6.80 | 5.5 ± 1.9 | 100 | 32 | 0.82 |
| 15$^a$ | 1 | 2.5 ± 0.5 | 98.4 | 39 | 0.91 |
| 16$^b$ | 1.28 | 3.9 ± 1.4 | 100 | 31 | 0.68 |

$^a$Commercial catalyst.
$^b$Catalyst reduced with H$_2$ during synthesis.
The rest of catalysts (11 to 14) were reduced with 1-phenyl ethanol.

Examples 17 to 22 (According to the Invention)

Au/CeO$_2$ catalysts were prepared with different amounts of Au. A higher amount of gold on ceria leads to a higher conversion. The oxidation efficiency increases until Au loading is between 1 and 2% wt.

TABLE 5

Catalytic activity of Au/CeO$_2$ with different gold loading after 9 hours test in 7 wt % tBuOOH/cyclohexane

| Example | Au loading (% wt) | Conversion (%) | Efficiency (%) | K/A Ratio |
|---|---|---|---|---|
| 17 | 0.22 | 85.52 | 32 | 1.14 |
| 18 | 0.52 | 94.36 | 32 | 1.01 |
| 19 | 1.13 | 94.96 | 35 | 0.87 |
| 20 | 2.13 | 98.79 | 34 | 0.83 |
| 21 | 5.80 | 100 | 29 | 1.17 |
| 22 | 7.82 | 100 | 26 | 1.25 |

Examples 23 to 26 (According to the Invention)

The impact of the morphology of $CeO_2$ as support for Au nanoparticles was evaluated. Three well-defined structure directed $CeO_2$ nanocrystal octahedras, rods and cubes, were synthesized. The most active catalyst per Au amount is the cube-shape one and it seems to be slightly more efficient for cyclohexane oxidation. For other catalysts, the efficiency lies in the range 0.32-0.35 which is similar to $Au/CeO_2$ with an amorphous support.

TABLE 6

Catalytic activity of Au nanoparticles on CeO2 with different surface morphology after 1.5 hours test in 7 wt % tBuOOH/cyclohexane

| Example | Support morphology | BET surface area (m²/g) | Au loading (wt.-%) | Au particle size (nm) | Conversion (%) | Efficiency (%) | K/A Ratio |
|---|---|---|---|---|---|---|---|
| 23 | Cubes | 31 | 0.44 | 2.9 ± 0.5 | 90.3 | 39 | 0.71 |
| 24 | Octahedra | 65 | 0.81 | 3.1 ± 0.4 | 94.6 | 35 | 0.76 |
| 25 | Rods | 111 | 0.98 | 2.3 ± 0.6 | 98.3 | 32 | 0.84 |
| 26 | $CeO_2$ | 222 | 1.15 | — | 97.30 | 32 | 0.85 |

Examples 27 to 28 (According to the Invention)

The tests of Au/MgO catalysts exhibit interesting properties as the catalyst is quite active at low Au content of 0.11 wt %. The table 6 below clearly shows the impact of gold particles size on the oxidation efficiency. The smaller the particles are, the higher is the efficiency.

TABLE 7

Catalytic performance of Au/MgO after test 9 hours in 7 wt % tBuOOH/cyclohexane

| Example | Au loading % (wt) | Au particle size (nm) | Conversion (%) | Efficiency (%) | K/A ratio |
|---|---|---|---|---|---|
| 27 | 0.11 | 2.9 +/− 2.0 | 97.2 | 35 | 1.12 |
| 28 | 1.31 | 14.3 +/− 7.2 | 98.7 | 22 | 0.82 |

After it has been confirmed that gold catalysts are able to oxidize cyclohexane by tBuOOH, we studied the catalysts in the target reaction that is oxidation of Cyclohexane by CyOOH.

In this case, it is more difficult to discriminate the products coming from cyclohexane oxidation and those coming from CyOOH decomposition. In fact it could be concluded that oxidation takes place if efficiency is higher than 100%.

Examples 29 to 32 (According to the Invention)

Au particles on different supports were tested in cyclohexyle hydroperoxide decomposition. In this case, it is possible to discriminate CyOOH decomposition from cyclohexane oxidation thanks to K/A-Oil yield. If K/A-oil yield is higher than 100%, it means that cyclohexane has been oxidized, whereas a yield lower than 100% leads to the conclusion that oxidation did not take place. As can be seen in the following table, the catalysts were active and efficient for this reaction except the Au/MgO which exhibited a much lower activity compared to what is obtained in tBuOOH decomposition. All these catalysts presented a high efficiency for cyclohexane oxidation with the yields lying between 111% and 116%.

TABLE 8

Catalytic performance of gold nanoparticles on different supports after 3 hours test in 6 wt % cyclohexyle hydroperoxide in cyclohexane

| Example | Catalyst | Support BET area (m²/g) | Au loading (wt.-%) | Au particle size (nm) | Conversion (%) | Efficiency (%) | K/A Ratio |
|---|---|---|---|---|---|---|---|
| 29 | $Au/TiO_2$ | 262 | 1.27 | 3.9 +/− 1.4 | 93.34 | 115 | 0.60 |
| 30 | $Au/CeO_2$ | 221 | 1.15 | — | 100 | 116 | 0.59 |
| 31 | $Au/CeO_2$ rods | 111 | 0.97 | 2.3 +/− 0.6 | 100 | 111 | 0.53 |
| 32 | $Au/ZrO_2$ | 240 | 1.02 | 2.2 +/− 0.8 | 90.12 | 113 | 0.48 |

Example 33 to 34

To finish with, we tested the impact of temperature. As expected, the catalyst is less active at 70° C. We also observe a decrease of efficiency when temperature decreases. At 70° C., cyclohexane oxidation is not observed.

TABLE 9

Catalytic performance of commercial 1% Au/TiO$_2$ after 4 hours test in 4.8 wt % cyclohexyle hydroperoxide in cyclohexane

| Example | Temperature (° C.) | Conversion (%) | Efficiency (%) | K/A ratio |
|---|---|---|---|---|
| 33 | 70 | 80 | 100 | 0.54 |
| 34 | 100 | 97 | 105 | 0.61 |

Example 35 to 38

In order to study the impact of the catalyst on by-product selectivity, we determined the yield of by-products for gold catalysts on different supports. The by-products yields lie between 4.5% and 6.3%. As a comparison, we also studied the selectivity of CeO$_2$ alone. As can be seen, CeO$_2$ is much less selective compared to Au supported catalyst. Thus, the use of Au catalyst improves by-products selectivity compared to CeO$_2$.

TABLE 10

Conversion, efficiency and byproducts formed in the deperoxidation of cyclohexyl hydroperoxide solution 5% with Au-based catalysts and CeO$_2$. Reaction time 3 h, 100° C.

| Example | Catalyst | % Au (wt) | Conversion (%) | Efficiency (%) | Byproducts (%) |
|---|---|---|---|---|---|
| 35 | Au/CeO$_2$ Rods | 1 | 100 | 111 | 5.7 |
| 36 | Au/ZrO$_2$ | 1.5 | 97 | 113 | 6.3 |
| 37 | Au/TiO$_2$ | 1.5 | 93 | 115 | 4.5 |
| 38 | CeO$_2$ | — | 100 | 106 | 8 |

Examples 39 to 44

We also studied the impact of radical scavengers on by-products selectivity. Thus, the use of hydroquinone enables to reduce the by-products yields of Au supported catalyst.

TABLE 11

Conversion, efficiency and byproducts formed in the deperoxidation of cyclohexyle hydroperoxide solution 5% after 3 h at 100° C. in the presence and in the absence of 10 wt % (based on the weight of the solution) hydroquinone

| Example | Catalyst | % Au (wt) | Scavenger | Conversion (%) | Efficiency (%) | Byproducts (%) |
|---|---|---|---|---|---|---|
| 39 | Au/CeO$_2$ | 1 | No scavenger | 99 | 111 | 8.3 |
| 40 | Au/CeO$_2$ | 1 | Hydroquinone | 94 | 82 | 3.2 |
| 41 | Au/ZrO$_2$ | 1.5 | No scavenger | 97 | 113 | 6.3 |
| 42 | Au/ZrO$_2$ | 1.5 | Hydroquinone | 99 | 112 | 1.5 |
| 43 | Au/TiO$_2$ | 1.5 | No scavenger | 93 | 115 | 4.5 |
| 44 | Au/TiO$_2$ | 1.5 | Hydroquinone | 89 | 116 | 1.7 |

The invention claimed is:

1. A method of oxidizing a cycloalkane to form a product mixture comprising a corresponding alcohol and a corresponding ketone, the method comprising:
   contacting the cycloalkane with a hydroperoxide compound in the presence of a heterogeneous catalyst comprising gold supported on an oxide to form the product mixture by oxidation,
   wherein the oxidation takes place in a reaction mixture comprising the cycloalkane and the hydroperoxide and at a temperature in the range of from 80° C. to 110° C., and wherein the oxide is selected from the group consisting of TiO$_2$, ZnO, MgO, CeO$_2$, and ZrO$_2$, and wherein the reaction mixture further comprises a radical scavenger.

2. The method of claim 1, wherein the cycloalkane is cyclohexane, the corresponding alcohol is cyclohexanol, and the corresponding ketone is cyclohexanone.

3. The method of claim 1, wherein the hydroperoxide compound is a compound of formula (I)

$$R\text{—}O\text{—}O\text{—}H \quad (I)$$

wherein R is a hydrocarbon group comprising from 1 to 15 carbon atoms.

4. The method of claim 3, wherein the hydrocarbon group is an alkyl group or an aryl group.

5. The method of claim 1, wherein the hydroperoxide compound is cyclohexyl hydroperoxide or tert-butylhydroperoxide.

6. The method of claim 1, wherein the reaction temperature is within the range of from 85° C. to 105° C.

7. The method of claim 1, wherein the product mixture comprises less than 7 wt.-% of byproducts formed during the reaction, relative to a total weight of the product mixture.

8. The method of claim 1, wherein the heterogeneous catalyst comprises 0.01 to 10 wt.-% of gold, based on the total weight of the heterogeneous catalyst.

9. The method according to claim 1, wherein the conversion of the reaction is in the range of from 50 to 100%.

10. The method of claim 2, further comprising oxidizing the cycloalkanol and the cyclohexanone in the product mixture with nitric acid to form adipic acid.

11. A method for converting a cycloalkane into the corresponding cycloalkanol, comprising:
   contacting the cycloalkane with a heterogeneous catalyst comprising gold supported on a oxide, wherein the oxide is selected from the group consisting of ZnO, MgO, CeO2.

12. A method for oxidizing a cycloalkane, comprising:
   contacting the cycloalkane with a heterogeneous catalyst comprising gold supported on a oxide, wherein the oxide is selected from the group consisting of ZnO, MgO, CeO2.

13. A method of oxidizing a cycloalkane to form a product mixture comprising a corresponding alcohol and a corresponding ketone, the method comprising:
contacting the cycloalkane with a hydroperoxide compound in the presence of a heterogeneous catalyst comprising gold supported on an oxide to form the product mixture by oxidation,
wherein the oxidation takes place in a reaction mixture comprising the cycloalkane and the hydroperoxide and at a temperature in the range of from 80° C. to 110° C., and wherein the oxide is selected from the group consisting of $ZnO$, $MgO$, $CeO_2$, and $ZrO_2$.

* * * * *